(12) United States Patent
Binder

(10) Patent No.: US 6,413,082 B2
(45) Date of Patent: Jul. 2, 2002

(54) ORTHODONTIC APPLIANCE FOR THE FORWARD DISPLACEMENT OF THE LOWER JAW

(75) Inventor: Friedrich Binder, Kieselbronn (DE)

(73) Assignee: Dentaurum J. P. Winkelstroeter KG, Ispringen (DE)

(*) Notice: Subject to any disclaimer, the term of this patent is extended or adjusted under 35 U.S.C. 154(b) by 0 days.

(21) Appl. No.: 09/785,961

(22) Filed: Feb. 16, 2001

Related U.S. Application Data

(63) Continuation of application No. PCT/EP99/06071, filed on Aug. 19, 1999.

(30) Foreign Application Priority Data

Aug. 19, 1998 (DE) .......................................... 198 37 555

(51) Int. Cl.$^7$ ................................................ A61C 3/00
(52) U.S. Cl. ........................................ 433/19; 433/18
(58) Field of Search .............................. 433/18, 19, 21, 433/22

(56) References Cited

U.S. PATENT DOCUMENTS

| 4,462,800 A | | 7/1984 | Jones | 433/19 |
| 4,708,646 A | | 11/1987 | Jasper | 433/19 |
| 5,183,388 A | | 2/1993 | Kumar | 433/19 |
| 5,378,147 A | * | 1/1995 | Mihailowtsch | 433/19 |
| 5,620,321 A | * | 4/1997 | Thornburg et al. | 433/19 |
| 5,632,618 A | | 5/1997 | Jensen | 433/19 |
| 5,829,975 A | * | 11/1998 | Gold | 433/19 |

* cited by examiner

Primary Examiner—John J. Wilson
(74) Attorney, Agent, or Firm—Leydig, Voit & Mayer, Ltd.

(57) ABSTRACT

In an orthodontic appliance, referred to as Herbst hinge, for the forward displacement of the lower jaw of a patient, with a pair of telescopes, each comprising a telescopic tube and a telescopic slide rod, which are attachable at their free ends in each case via a joint to the patient's upper jaw and lower jaw, respectively, for increasing the freedom of movement of the lower jaw while at the same time achieving the therapeutically desired forward push onto the lower jaw, it is proposed that the telescopes in the telescoped state be rigid, as known per se, but in the extended state be flexible.

16 Claims, 2 Drawing Sheets

ORTHODONTIC APPLIANCE FOR THE FORWARD DISPLACEMENT OF THE LOWER JAW

Figure 1A:
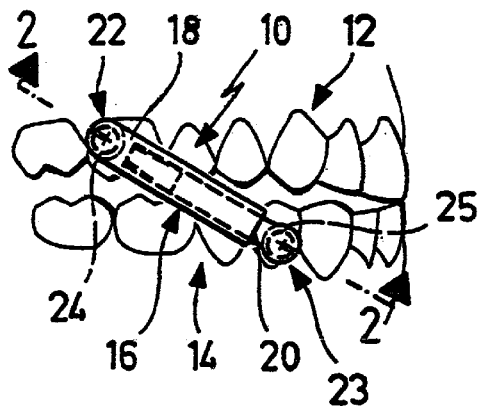

The present disclosure is a continuation of the subject matter disclosed in international application PCT/EP99/06071 of Aug. 19, 1999, the entire specification of which is incorporated herein by reference.

The invention relates to an orthodontic appliance for the forward displacement of the lower jaw of a patient, which is usually referred to as Herbst hinge.

Such appliances comprise a pair of telescopes, which each consist of a metal telescopic tube and a metal slide rod guided therein, and which are attached on both sides of the patient's jaw, for example, via orthodontic bands, to the patient's upper and lower jaws.

The appliance known in the literature as Herbst hinge can be compared to an artificial joint between upper jaw and lower jaw (H. Pancherz, Kleines Lehrbuch der Angle-Klasse II,1 unter besonderer Berücksichtigung der Behandlung, Chapter 16, pages 225 to 251, Quintessenz Verlags-GmbH, Berlin). When the jaw is closed the telescopes are retracted or telescoped fully, and the Herbst hinge can thus apply therapeutically desired forward pushing forces to the lower jaw.

When the patient opens his jaw the slide rod travels a certain distance out of the telescopic tube and thus allows the patient limited space for his jaw movements. Owing to the rigidity of the metallic telescopic tubes and slide rods, the Herbst hinge is, however, relatively rigid and results in considerable limitation of the freedom of movement of the lower jaw. If the appliance is inappropriately fitted undesirably large forces can also be exerted on the jaw or the appliance can be even be destroyed as a result of this.

As a rule, the Herbst hinge is designed as a so-called firmly attached fixture in order to permanently exert the necessary forward pushing force on the lower jaw during the treatment. However, it is not possible for the patient to briefly remove the appliance to clean it for oral hygiene purposes.

Different solutions for attaching the telescopes to the upper and lower jaws have been discussed in the literature. For example, the textbook cited above describes the attachment by screws to attachment parts affixed to the molars of upper and lower jaws, as does U.S. Pat. No. 4,462,800. Another solution which works with a pinning together is known from U.S. Pat. No. 5,183,388. Attachment of the telescopic rods to the molars by ball pins and securing rings is recommended in PCT/DK94-00183.

All these solutions have the disadvantage that the attachment elements (e.g. screws, pins, securing rings) naturally have to be very small, which makes it difficult even for experienced staff to insert or remove the Herbst hinge, and in individual cases these small parts, if handled clumsily, can be swallowed by the patient.

The object of the invention is to further develop an appliance of the kind described at the outset so that while the therapeutically desired forward push on the lower jaw remains ensured, a greater freedom of movement is imparted to the lower jaw.

This object is accomplished in accordance with the invention with the appliance described at the outset in that the telescopes in the telescoped state are rigid, as known per se, but in the extended state are flexible.

This constructional principle ensures that in the closed state of the jaw (simultaneously the retracted or telescoped state of the telescopes) the desired forward pushing forces can act, but accord the lower jaw of the patient to be treated a considerably increased freedom of movement when he opens his jaw (forward pushing forces are not active here with the Herbst hinge).

A specific embodiment of this principle consists in that the telescopic tubes are of rigid design, but the telescopic rods are elastically deformable.

As an alternative thereto, in another embodiment the slide rod can also be of rigid design, but the section guided in the telescopic tube includes a conical area. Herein, as soon as the slide rod is moved a certain length out of the telescopic tube, the play between the telescopic tube and the slide rod increases, which increases the freedom of movement of the lower jaw. If, in addition, the slide rods are produced from an elastically deformable material, a particularly good effect is achieved with respect to increasing the freedom of movement of the lower jaw.

The conical area preferably extends over at least one fourth of the length of the telescoping sections of the slide rods. Thus, more freedom of movement is already created for the lower jaw at a relatively early stage of opening the jaw.

An angle of taper of approximately 2° is already sufficient for a noticeable increase in the freedom of movement. As a rule, a maximum angle of taper of approximately 15° is adequate to accord highly improved wearing comfort to the patient. On the other hand, a limitation of the angle of taper to 15° eliminates the danger of the slide rod tilting in the telescopic tube and exposes in the extended state of the telescope only a small cross-sectional area of the mouth of the telescopic tube, through which undesired materials such as, for example, bits of food, etc., can penetrate into the telescope so that this limit is also recommended from the point of view of oral hygiene.

In general, materials whose modulus of elasticity in tension lies in the range of from 100 N/mm$^2$ to 20,000 N/mm$^2$ are suitable for the manufacture of the inventive telescopes.

In accordance with the present invention, plastic is a preferred material. It is not only easy to work to the required shapes, but also offers aesthetic advantages over telescopes made of metal. Both rigid and elastically deformable slide rods can be made of plastic. Plastic is also suitable for the manufacture of telescopic tubes. In the case of the latter, it is recommended, in particular, to use transparent plastic, which not only allows checking of the choice of the correct length of the slide rods, but, in addition, also checking as to the cleanliness and the oral hygienic state of the telescopes, in particular, the interior of the telescopic tube. Preferred elastic plastic materials are those of the polyolefins, EVAs and polyamides. These plastic materials have a modulus of elasticity in tension in the range of approximately 500 to 2,500 N/mm$^2$ (German Industrial Standard 53457) and do not exhibit any breakage in the impact test (German Industrial Standard 53453). Moreover, these plastic materials allow an elastic deflection of the slide rods and/or telescopic tubes without any noticeable deformation remaining after the deflection.

Ball joints are also preferably used in the present invention for attaching the telescopes to upper and lower jaws. Here a ball head attached to the tooth serves for support on the jaw, while a ball socket formed in each case at one end of slide rod and telescopic tube engages over this ball head. The ball socket is preferably of elastic resilient design so that it is snappable onto the associated ball head.

The snapping of the ball socket onto the associated ball head is facilitated by the choice of a sufficiently elastic plastic material. However, limits are set here as the ball socket must be inherently stable enough for it to transmit the correcting forces unadulterated onto the ball head.

Alternatively, the ball socket can be provided with one or several radially extending slots which extend as far as the mouth opening of the socket. In this case, a stiffer plastic material can then be used.

Finally, it is to be ensured that the holding forces between ball head and ball socket are large enough for unintentional detachment of the snap connection to be avoided.

Again the use of plastic for the fabrication of the slide rods and the telescopic tubes, which, in this case, are integrally formed with the ball sockets is favorable for this construction. However, the use of metals which are generally recognized as safe from the point of view of oral hygiene, such as, for example, nickel-free steels or titanium, is recommended for the ball heads. Not only do metallic ball heads better resist the forward pushing forces which they are to transmit onto the lower jaw, but they are also easier to attach with the necessary security, for example, by means of metallic tooth bands, to the patient's teeth.

A continuous opening in the interior of the telescopic tubes, which leads to the cavity of the ball socket, serves to facilitate cleaning of the telescopes. Foreign matter which has unintentionally penetrated into the telescopic tube can thus also be easily flushed out by the patient himself, and the telescopes can be kept in perfect condition as regards oral hygiene by the patient himself. Here it is, of course, helpful for the telescopic tubes, as already mentioned further above, to be made of transparent plastic.

Provision is made in a preferred embodiment for the telescopic tubes to have in their interior a stop for maximum slide-in of the slide rods. When the telescope is retracted, which results in transmission of the forward pushing forces, the corresponding end of the slide rod is supported on the stop, and the slide rod is thus prevented from being pushed in too far, which could result in jamming of the free end of the slide rod. Moreover, this also ensures that the therapeutically desired forward pushing forces are maintained when the telescope is in the retracted or telescoped state.

In addition, provision may be made for spacers forming the stop to be inserted into the interior of the telescopic tube so as to alter the forward pushing forces during the patient's treatment, or to adapt the length of the telescope in the retracted or telescoped state to the treatment success which has already occurred. Alternatively, this can, of course, also be done by adapting or exchanging slide rods of a different length.

As known per se, the transmission of forces can also take place via a stop which is arranged at the end of the telescopic slide rod adjacent to the ball socket. This stop is then supported at the free end of the telescopic tube.

Figure 1B:
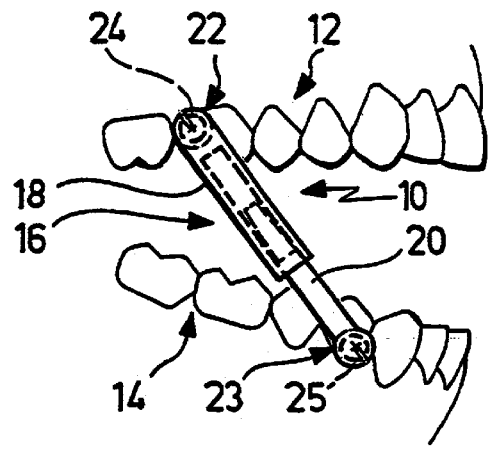
Figure 2:
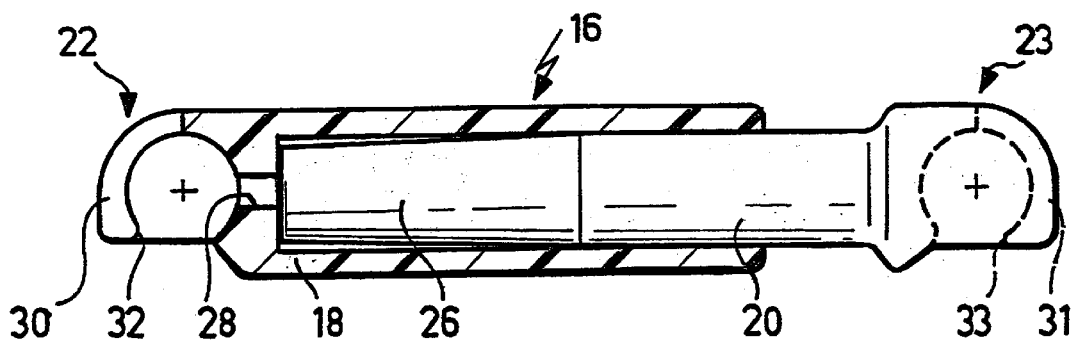
Figure 3:
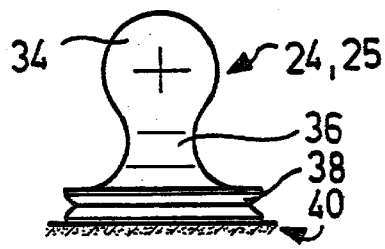
Figure 4:
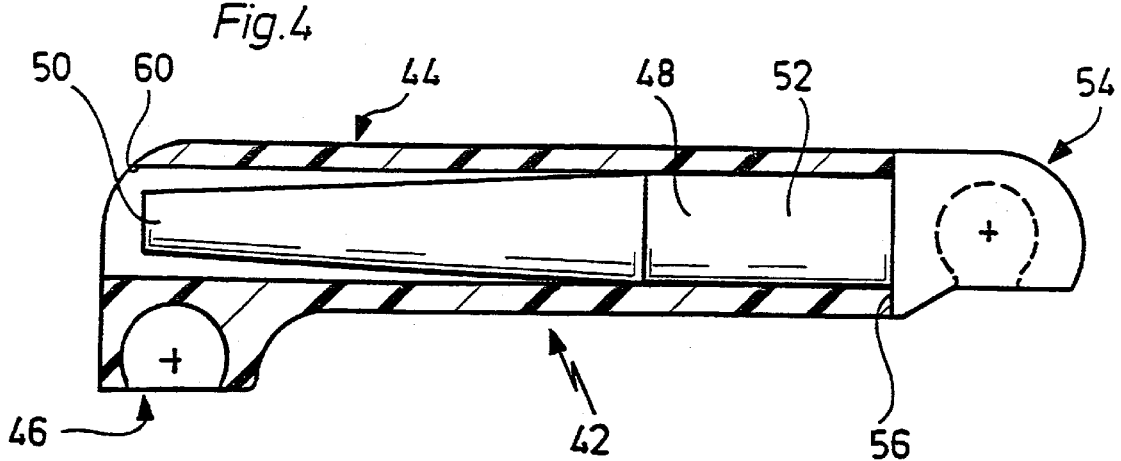
Figure 5:
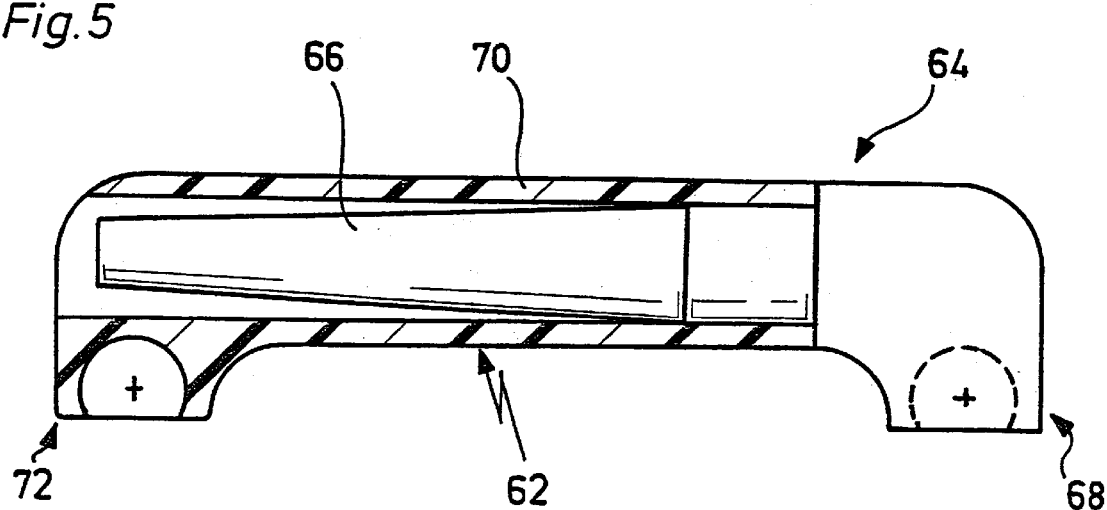
Figure 6:
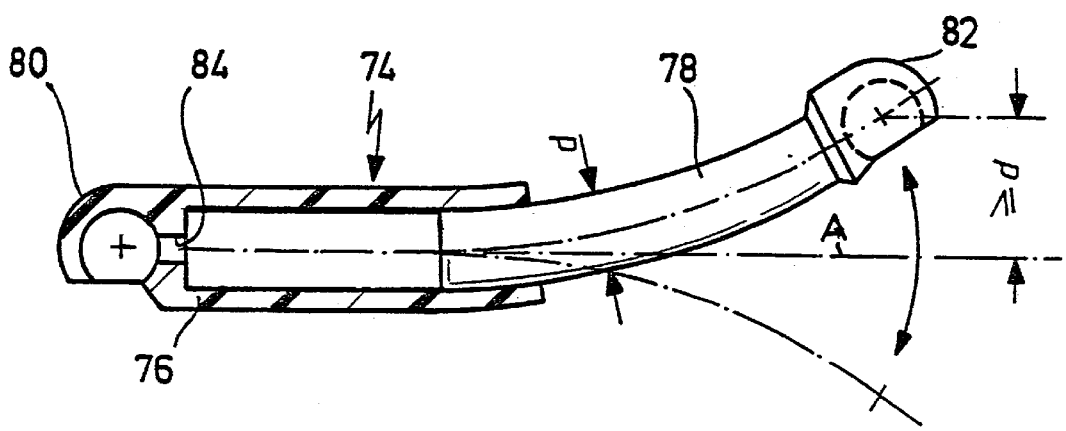

These and further advantages of the invention are the subject matter of the subclaims and will be explained in further detail hereinbelow with reference to the drawings, which individually show:

FIGS. 1 a) and b) a schematic representation of the way in which an orthodontic appliance according to the invention function;

FIG. 2 a section along cutting line 2—2 in the orthodontic appliance of FIG. 1 a) according to a first embodiment;

FIG. 3 a ball head for attachment of the orthodontic appliance according to the invention to the tooth of a patient;

FIG. 4 a sectional view of a second embodiment of the orthodontic appliance according to the invention;

FIG. 5 a sectional view of a third embodiment of the orthodontic appliance according to the invention; and FIG. 6 a sectional view of a fourth embodiment of an orthodontic appliance according to the invention.

FIG. 1a) shows an inventive orthodontic appliance designated by reference numeral 10 (referred to hereinafter as Herbst hinge), which is attached at one end to an upper jaw 12 and at another end to the lower jaw 14 of a patient. The Herbst hinge is attached in pairs on both sides of the upper and lower jaws of the patient and serves to forwardly displace the lower jaw of the patient.

The inventive Herbst hinge 10 comprises as main components a telescope 16 with a telescopic tube 18 and a telescopic slide rod 20.

One end of the telescope 16 is joined to the upper jaw 12 and one end to the lower jaw 14.

For this purpose, the telescope 16 comprises at each end, in one case in continuation of the telescopic tube 18, a ball socket 22, and, in the other case in continuation of the telescopic slide rod 20, a ball socket 23, which can snap onto ball heads 24, 25, each attached to a tooth of the upper jaw 12 and the lower jaw 14, respectively.

The ball heads 24, 25 are usually welded onto so-called orthodontic bands, and the bands are fitted onto the tooth intended for the support. The orthodontic bands are not shown in FIGS. 1a) and 1b).

When the patient's jaw is in the closed state (see FIG. 1a)) a forward pushing force for forward displacement of the patient's lower jaw 14 is generated by the telescope 16 pushed together as far as the stop, so that upper jaw and lower jaw are arranged in the desired, ideal location relative to each other.

On opening the jaw (cf. FIG. 1b)), the telescope 16 is extended, i.e., the telescopic rod 20 moves partially out of the telescopic tube 18, and, of course, correction forces are no longer active in this state.

The embodiment of the telescope 16, shown scaled-up in FIG. 2, comprises in accordance with the invention, at the end of the telescopic slide rod 20 arranged telescopically in the telescopic tube 18 a conically tapering section 26, which extends over more than half the length of the part of the telescopic slide rod 20 received in the telescopic tube 18 in the retracted or telescoped state. The angle of taper here is approximately 10°.

The telescopic tube 18 comprises at its end adjacent to the ball socket 22 a bottom with an opening 28, which connects the volume of the ball socket 22 with the interior of the telescopic tube 18. It is thereby made possible to clean the interior of the telescopic tube 18 in a simple way, and, in particular, to easily flush out deposits which may develop in the interior of the telescopic tube 18 in the course of use of the Herbst hinge.

The two ball sockets 22 and 23 comprise in the plane of the longitudinal axis of the telescope 16 a slot 30, 31 running in a radial direction and extending from a respective mouth opening 32, 33 of the sockets 22, 23 around approximately half of a circumferential circle of the ball socket cross section.

These slots 30, 31 simplify the snapping of the ball sockets onto the associated ball heads 24, 25.

Finally, FIG. 3 shows such a ball head 24, 25, by way of example, which comprises a ball portion 34, which is held by way of a neck 36 on a base 38. This base 38 serves for adherence or welding to an orthodontic band 40, which is only outlined in FIG. 3.

As described above, the design of the slide rod 20 with the conical area 26 allows, even when the patient's mouth opens slightly and, as a result, the telescope 16 is extended, not only a mesial movability of the lower jaw, but jaw movements in the direction transverse thereto are also significantly facilitated. The ball head/ball socket joints also contribute to this to a certain extent.

If, in addition, the telescopic slide rod 20 is made of an elastic material, there is a further reduction in the limitation of the movability of the lower jaw, and there is an increase in the wearing comfort for the patient. In the retracted state of the telescope 16 (cf. FIGS. 1a) and 2), however, a sufficiently stiff structure is obtained, as the telescopic tube 18 additionally supports the slide rod 20 and substantially excludes elastic deformations of the latter. In spite of the considerably increased movability of the Herbst hinge in the extended state, when the jaw is closed, i.e., when the telescope is pushed together, an exact transmission of force onto the lower jaw, which is comparable with the conventional Herbst hinges, is thereby achievable.

Owing to the simple snap mechanism, the patient himself can remove the Herbst hinge to take care of his teeth and hygienically treat the Herbst hinge as such, and he can also mount it again. Moreover, the use of small parts, which even create handling problems for experienced users, is dispensed with when mounting the Herbst hinge.

This additionally results in shorter treatment times, also when the dentist is carrying out a check-up.

It is particularly advantageous for the telescopic tube 18 to be made of transparent plastic as the correct choice for the telescopic rod 20 can then be made very easily when the Herbst hinge is in the assembled state. The manufacture of the telescopic rod 20 from plastic has the additional advantage that prefabricated lengths can be shortened relatively easily by the doctor in charge, so that an optimal length of the slide rod 20 can be used for the initially targeted treatment success without a plurality of slide rods of different lengths having to be kept in stock.

An alternative procedure to this would be to use slide rods of a constant length, but with progressive treatment success to insert into the interior of the telescopic tube 18 further stops, for example, in the form of rings, which successively shorten the insertion length of the telescopic slide rod 20 into the tube 18 concomitantly with the treatment success.

Here, again, the transparent design of the telescopic tube 18 also is an aid, by means of which it is very easy to check whether the fixing of the stop for the telescopic slide rod 20 has been chosen correctly.

The manufacture from a plastic material has the further advantage that the components can be manufactured much more economically than corresponding metal components, and in the event of wear or the like, these can also be exchanged without any great expense in the course of the treatment. The wearing comfort is significantly improved by the flexible design of the telescope 16, and there is virtually no impairment in the perception of oral hygiene by the patients since they themselves can remove the Herbst hinge briefly for this purpose and can affix it again themselves. This has, in particular, to do with the fact that additional securing means are not necessary, and the Herbst hinges can simply be snapped onto the ball heads which remain firmly mounted on the teeth.

If excessively high forces are applied to the connection points of the Herbst hinge with the upper and lower jaws, the appliance can unclip itself so that here, too, damage to the Herbst hinge or the teeth can be safely avoided.

If the Herbst hinge is made from a plastic material, an economical production in an injection molding tool presents itself. Moreover, the metal parts which are worn in the mouth are further reduced to a significant extent by manufacturing the Herbst hinge from plastic. The spatial conditions of the patients' upper and lower jaws can be taken into account by necks 36 of the ball heads 24, 25 differing in length.

In FIG. 4 a second embodiment of the invention is shown, in which a telescope 42 comprises a telescopic tube 44, which has at one end a ball socket 46 protruding in a radial direction (in FIGS. 1 and 2 an embodiment is shown in which the ball socket adjoins the telescopic tube in an axial direction). A telescopic slide rod 48 pushed fully into the telescopic tube 44 comprises at its free end a conical area 50 which extends over approximately two-thirds of the length of the slide rod and is adjoined by a cylindrical area 52 and (in this sequence) a ball socket 54. The ball socket 54 here is arranged in axial continuation of the cylindrical area 52.

The ball socket 54 adjoins the cylindrical area 52, and the latter is radially recessed (recess 56) in relation to the ball socket 54. In the fully inserted state, the recess 56 abuts the free end of the telescopic tube 44 and thereby forms a stop.

The end opposite the free end of the telescopic tube comprises an opening 60 which exposes the interior of the telescopic tube over the full cross section. This makes it possible for the telescope to be cleaned with particularly great ease.

The ball sockets 46 and 54 can be designed in analogy with the embodiments described in conjunction with FIGS. 1 and 2.

Differently from the second embodiment shown in FIG. 4, the embodiment of an inventive telescope 62 shown in FIG. 5 comprises a telescopic slide rod 64, which includes a conical area 66 which extends almost over the entire length of the retracted telescopic rod component. Furthermore, the ball socket 68 arranged on the telescopic slide rod herein is arranged so as to protrude radially from the slide rod and hence symmetrically in relation to the ball socket 72 protruding form the telescopic tube 70. In this embodiment, too, the end of the telescopic tube 70 adjacent to the ball socket 72 is of open design so that any bits of food etc. which may have penetrated into the telescope can be removed without any trouble.

An embodiment of the inventive telescope, which is based on the first embodiment described in conjunction with FIGS. 1 and 2, is shown in FIG. 6. Herein, the telescope 74 comprises a telescopic tube 76 and telescopic slide rod 78, which carry ball sockets 80, 82 adjoining oppositely arranged ends in an axial direction. The telescopic tube interior is again connected by a continuous bore 84 to the cavity of the ball socket 80 to improve the possibility of cleaning it.

Differently from the embodiment of FIGS. 1 and 2, the telescopic slide rod 78 does not have any conical area, but has a constant diameter essentially over its entire length. Here, however, an elastic plastic material is used for the manufacture of the telescopic rod 78, which allows a deflection of the telescopic slide rod at the ball socket end from the axial direction A through at least the diameter d. This dimension applies to the case where the telescopic slide rod 78 is extended to a maximum permissible extent.

In this embodiment, the improved wearing characteristic, i.e., the increased movability of the lower jaw, is guaranteed solely by the choice of material for the manufacture of the slide rod 78. In the present case, a polypropylene material with a modulus of elasticity in tension of approximately 1,500 N/mm$^2$ was used. The slide rod 78 can be deflected as shown without any deformations remaining after its return being observed.

This choice of material can, of course, be combined with the conical design of the free end of the slide rod, as illustrated in FIGS. 2, 4 and 5.

What is claimed is:

1. An orthodontic appliance attachable to a patient's upper and lower jaws for the forward displacement of the lower jaw of the patient, the appliance comprising a pair of telescopes, each said telescope having two free ends and comprising a telescopic tube and a telescopic slide rod, and joints for attaching each said telescope at their free ends to the patient's upper jaw and lower jaw, respectively, the telescopes in the retracted state being rigid and in the extended state being flexible.

2. The appliance as defined in claim 1, wherein the telescopic tubes are of rigid design and the slide rods of elastically deformable design.

3. The appliance as defined in claim 2, wherein the slide rods are made of an elastically deformable plastic material whose modulus of elasticity lies in the range of from 500 $N/mm^2$ to 2,500 $N/mm^2$.

4. The appliance as defined in claim 1, wherein the slide rods each have an end and a telescoping section telescopically disposed in the respective telescoping tube, said telescoping sections having a conical area at said ends telescopically disposed in the telescopic tubes.

5. The appliance as defined in claim 4, wherein the conical areas of the slide rods extend over at least one fourth of the length of the telescoping section of the slide rods.

6. The appliance as defined in claim 4, wherein the telescoping sections each have an angle of taper, the angle of taper being in the range of from 2° to 15°.

7. The appliance as defined in claim 6, wherein the range is of from 5° to 10°.

8. The appliance as defined in claim 1, wherein the telescopic slide rods are made of a plastic material.

9. The appliance as defined in claim 1, wherein the telescopic tubes are made of a plastic material.

10. The appliance as defined in claim 9, wherein the telescopic tubes are made of a transparent plastic material.

11. The appliance as defined in claim 1, wherein the joints are ball joints and comprise a ball head adapted to be attached to a tooth of the patient, and a ball socket disposed at said free ends of the telescopic tubes and the telescopic slide rods, said ball socket being elastically resilient, and adapted to snappingly receive the associated ball head.

12. The appliance as defined in claim 11, wherein the ball sockets are integrally formed with the telescopic tubes and the telescopic slide rods.

13. The appliance as defined in claim 11, wherein the ball sockets each have an opening and a slot extending at a right angle to a circumferential line of the respective said opening.

14. The appliance as defined in claim 1, wherein each said telescopic tube has an interior bore in which the telescopic slide rods are telescopically disposed, respectively, the telescopic tubes each have an opening between the ball socket and the interior bores of the tubes.

15. The appliance as defined in claim 1, wherein each said telescopic tube has an interior bore in which the telescopic slide rods are telescopically disposed, respectively, the interior bores of the telescopic tubes each having a stop for delimiting the maximum distance the telescopic slide rods may telescope into said respective telescopic tube.

16. The appliance as defined in claim 3, wherein the stop is formed by exchangeable spacers.

* * * * *

UNITED STATES PATENT AND TRADEMARK OFFICE
CERTIFICATE OF CORRECTION

PATENT NO.    : 6,413,082 B2
DATED         : July 2, 2002
INVENTOR(S)   : Binder It is certified that error appears in the above-identified patent and that said Letters Patent is hereby corrected as shown below:

<u>Column 8,</u>
Line 30, "claim 3" should read -- claim 15 --.

Signed and Sealed this

Fifteenth Day of October, 2002

Attest:

Attesting Officer

JAMES E. ROGAN
*Director of the United States Patent and Trademark Office*